United States Patent

Beyer et al.

[11] 3,978,575
[45] Sept. 7, 1976

[54] METHOD AND DEVICE FOR EXTRACTING FILTER FRITS FROM LIQUID CHROMATOGRAPHIC COLUMNS

[75] Inventors: William F. Beyer, Portage; Harry S. Dankert, Kalamazoo, both of Mich.

[73] Assignee: The Upjohn Company, Kalamazoo, Mich.

[22] Filed: June 18, 1975

[21] Appl. No.: 587,827

[52] U.S. Cl. .............................. 29/427; 29/200 D; 29/234; 29/256; 29/270
[51] Int. Cl.² ....................................... B23P 19/02
[58] Field of Search ............ 29/426, 427, 234, 240, 29/256, 270, 271, 278, 280, 281, 282, 283, 200 D, 200 H, 244; 81/3 H, 53.2, 71; 210/496, 499, 510; 269/1, 3, 9

[56] References Cited
UNITED STATES PATENTS

| | | | |
|---|---|---|---|
| 2,670,639 | 3/1954 | Flowers et al. | 29/427 X |
| 3,120,700 | 2/1964 | Chuplis | 29/281 X |
| 3,740,814 | 6/1973 | Marshall | 29/200 D |

*Primary Examiner*—C.W. Lanham
*Assistant Examiner*—James R. Duzan
*Attorney, Agent, or Firm*—Woodhams, Blanchard and Flynn

[57] ABSTRACT

A method and apparatus for removing a small metal filter from a liquid chromatographic column, wherein a retaining member is clamped around the tube. A first centering device is releasably centered on the retaining member in alignment with the filter, whereupon a drill is slidably guided through the centering device for forming a hole of selected depth in the filter. The first centering device is removed and a second centering device is supported on the retainer, which second centering device has a threaded opening therethrough aligned with the filter. An extractor is threaded into the opening so that the end of the extractor is disposed directly adjacent the filter. A tapping unit having an elongated thread-forming tap is slidably inserted through an opening formed in the extractor, which opening is aligned with the hole formed in the filter. The tapping unit is threaded inwardly so that the tap threadably engages the filter and until a handle on the tapping unit abuts the extractor. The second centering device and the tapping unit are then held in a nonrotatable condition, and the extractor is reversely rotated so as to thread same out of the second centering device, whereby the tapping unit is axially displaced outwardly away from the second centering unit so that a pulling force is imposed on the filter to remove same from the end of the column.

7 Claims, 6 Drawing Figures

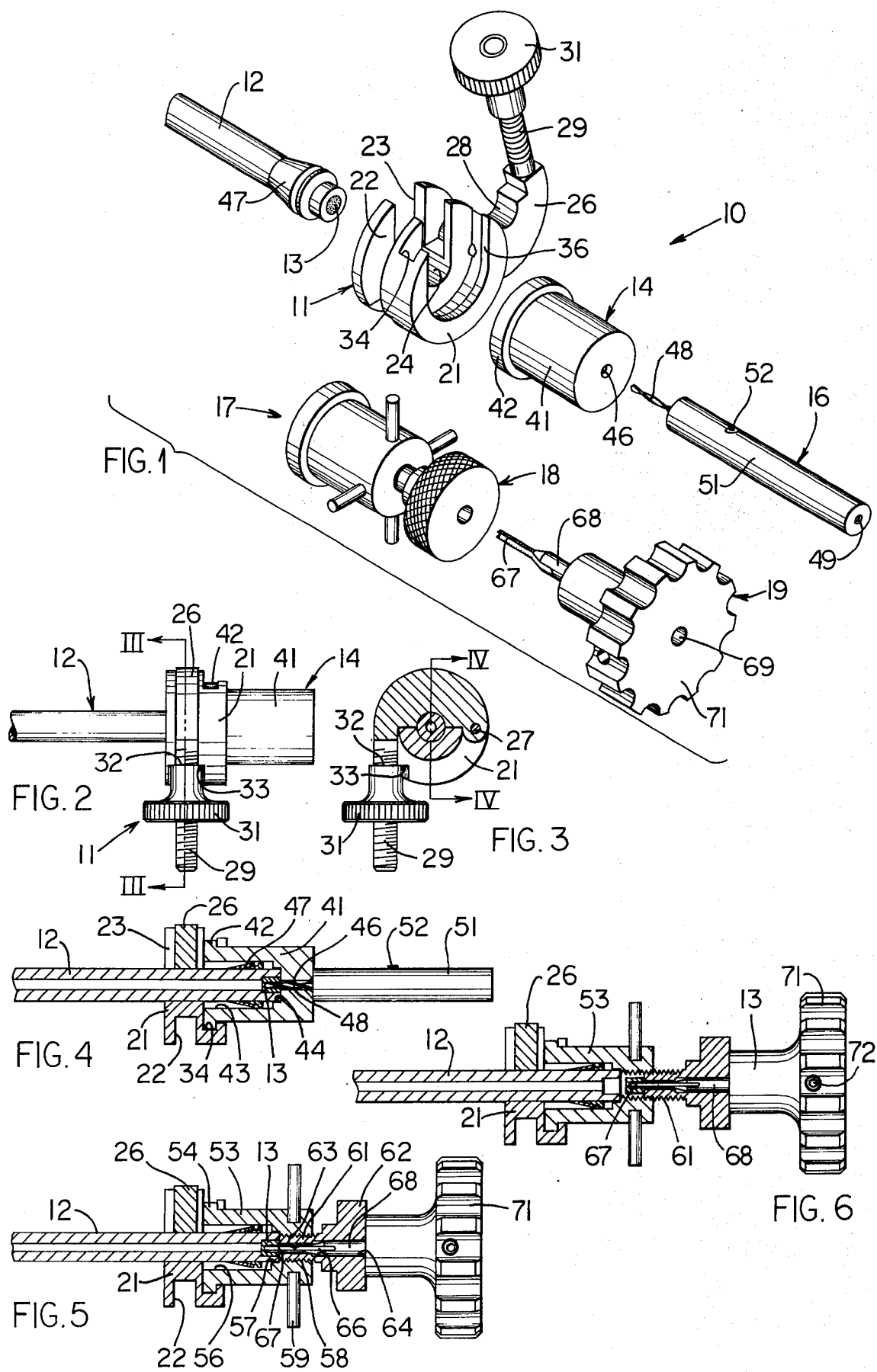

METHOD AND DEVICE FOR EXTRACTING FILTER FRITS FROM LIQUID CHROMATOGRAPHIC COLUMNS

FIELD OF THE INVENTION

This invention relates to a method and apparatus for removing a small metal filter frit from a tubular member, such as from a liquid chromatorgraphic column.

BACKGROUND OF THE INVENTION

The removal of metal filter frits used to retain packing materials in liquid chromatographic columns is frequently necessary, as when the frits become plugged, when new packing material is desired, or when a column void is suspected. This latter situation may be encountered rather frequently when high pressures, such as 3000 psig, are used within chromatographic column supports of small diameter. However, in view of the smallness of these frits, which frits are in the order of 0.125 inch, the removal of the frits has been an extremely difficult and often unsuccessful procedure. While various attempts have been made at devising an apparatus capable of removing this small frit from the tube or column, nevertheless all of these known devices have, to the best of our knowledge, been only partially successful in that they have not permitted the efficient removal of the frit in a safe and dependable manner. Further, none of the known devices can dependably remove the frit without causing damage to the tube or column. Thus, in view of the difficulties encountered in removing these frits, it has been a rather common practice to merely discard the complete column containing the frit therein when one of the above-mentioned conditions is encountered. This maintenance procedure, however, is obviously undesirable since these columns are relatively expensive and thus the need to replace these columns on a rather frequent basis substantially increases the overall operating cost of the chromotographic apparatus. Accordingly, the present invention relates to an improved method and apparatus for removing a small metal filter frit from a tube, such as a liquid chromatographic column, which method and apparatus permits the frit to be easily and efficiently removed from the column so as to permit reusage of the column after installation therein of a new packing and/or frit It is also an object of the present invention to provide a method and apparatus, as aforesaid, which is equally applicable for use on tubes or columns which permits removal of the metal frit from either end of the column, irrespective of whether or not the column has external ferrules thereon.

A further object of the present invention is to provide a method and apparatus, as aforesaid, which is extremely simple and is manually manipulated to provide for efficient yet precise removal of the frit from the column without damaging the column or the packing.

Other objects and purposes of the invention will be apparent to persons acquainted with devices of this type upon reading the following specification and inspecting the accompanying drawings.

BRIEF DESCRIPTION OF THE DRAWINGS

FIG. 1 is an exploded perspective view of the various components of the frit extracting device according to the present invention.

FIG. 2 is a side elevational view of the retainer and drill centering device mounted on the end of the column.

FIG. 3 is a sectional view taken along line III—III in FIG. 2.

FIG. 4 is a sectional view taken along line IV—Iv in FIG. 3 and illustrates the drilling of a hole in the frit.

FIG. 5 is a view similar to FIG. 4 and illustrating the attachment of an extracting device to the frit.

FIG. 6 is a view similar to FIG. 5 and illustrates the frit after extraction from the tube.

Certain terminology will be used in the following description for convenience in reference only and will not be limiting. For example, the words "upwardly", "downwardly", "leftwardly" and "rightwardly" will refer to directions in the drawings to which reference is made. The words "inwardly" and "outwardly" will refer to directions toward or away from, respectively, the geometric center of the device and designated parts thereof. Said terminology will include the words above specifically mentioned, derivatives thereof and words of similar import.

SUMMARY OF THE INVENTION

The objects and purposes of the invention are met by providing a cup-shaped drill guide which is slidably fitted over the end of a column containing a frit therein. A retainer is then moved transversely into engagement with the drill guide, which retainer includes a swingable clamping member for permitting the retainer to surround and clampingly engage the column to hold the drill guide thereon. A rotatable drill is guided through a small opening formed in the end wall of the drill guide for forming a small blind bore in the frit. The retainer is then released to permit removal of the drill guide from the column. A cup-shaped extractor guide is then positioned on the end of the column and secured thereto by the retainer. An extractor member is then threaded into an opening formed in the end wall of the extractor guide, which opening is aligned with but is larger in diameter than the frit. An elongated tap is fed through a central opening formed in the extractor member and is rotatably threaded into the frit until a handle on the tap abuts the outer end of the extractor member. The handle and the extractor guide are then maintained stationary, and the extractor member is rotated in a reverse direction to unthread same from the extractor guide, which in turn pulls the tap outwardly for removing the frit from the end of the column.

DETAILED DESCRIPTION

FIG. 1 illustrates therein the various components of a frit extracting Device 10 according to the present invention. The extracting device 10 includes a retainer 11 adapted to be clampingly engaged on a tube or column 12, which tube has a non-threaded frit or filter 13 mounted in the end thereof. A drill guide 14 is adapted to be positioned on the end of the tube and held thereon by the retainer 11, and a drill device 16 coacts with the guide 14 to permit the forming of a small hole or bore in the frit 13. An extractor guide 17 is also adapted to be mounted on the end of the tube 12 and held thereon by the retainer 11. The extractor guide 17 threadably receives therein a rotatable extractor member 18, which member in turn permits a tapping unit 19 to be inserted therethrough and threadably engaged with the frit 13. These components will be individually described below.

The retainer 11 comprises a substantially cylindrical member 21 which has an annular groove 22 formed therearound. The retainer member 21 also has a slot 23 extending axially thereof, which slot extends inwardly from the periphery of the retainer member and terminates in a semi-cylindrical wall 24 which is centered about the axis of the retainer member. An arcuate clamping member 26 is hinged to the retainer member 21 by the pin 27, whereby the clamping member 26 can be swingably moved into the annular groove 22 so as to close off the outer end of the slot 23. Clamping member 26 has a semi-cylindrical wall 28 thereon which is disposed directly opposite the semi-cylindrical wall 24 when the clamping member is in a closed position for permitting the tube 12 to be clamped between the walls 24 and 28 as illustrated in FIG. 3. A threaded rod 29 is fixed to and projects outwardly from the free end of the clamping member 26, which rod has a clamping knob 31 rotatably and threadably engaged thereon. The knob 31 has an end face 32 which is adapted to be moved into abutting and clamping engagement with an abutment surface 33 formed on the retainer member 21.

An enlarged outwardly opening recess 34 is formed in the retainer member 21 adjacent one end thereof, which recess 34 opens radially through the periphery of the retainer member and at its inner end terminates in a semi-cylindrical wall which is centered about the axis of the retainer member. A further slot 36 is formed in the end wall of the retainer member 21, which slot 36 extends through the end wall so as to be in open communication with the recess 34. The slot 36 has a configuration corresponding to but smaller than that of the recess 34. Slot 36 opens radially outwardly to the periphery of the retainer member and terminates in a semi-cylindrical wall which is centered about the axis of the retainer member.

Considering now the drill guide 14, same comprises a substantially cup-shaped cylindrical member 41 having an enlarged annular flange 42 adjacent one end thereof. The flange 42 has a diameter which is slightly less than the transverse width of the slot 34, and the axial thickness or width of the flange 42 is also slightly less than the axial width of the slot 34, so that the flange 42 can be inserted into and closely confined within the slot or recess 34. The cylinder 41 similarly has a diameter which is just slightly less than the transverse width of the slot 36 so that cylinder 41 will be positionable within and closely confined by the slot 36.

As shown in FIG. 4, a stepped opening means extends through the cylindrical member 41, which opening means includes an enlarged bore 43 which extends inwardly from one end of the cylindrical member and terminates in a reduced diameter bore 44. The end wall of the cylindrical member 41 has a further bore 46 of small diameter extending therethrough, which bore 46 is coaxially aligned with and in communication with the bores 43 and 44. The bore 44 is sized to snugly accommodate therein the end of the tube 12, whereas the enlarged bore 43 will accommodate any enlargement which may be on the end of the tube, such as a ferrule 47.

The small bore 46 is sized so as to slidably but freely accommodate and guide a drill 48 associated with the drill device 16. The drill 48 has the shank thereof positioned within an opening 49 which extends coaxially through an elongated substantially cylindrical holder 51. A conventional set screw 52 is provided for fixedly clamping the drill 48 to the holder 51. Set screw 52 also permits the axial position of the drill to be adjusted relative to the holder to thus vary the length of the drill which projects outwardly beyond the forward end of the holder.

Considering now the extractor guide 17 (FIG. 5), same comprises a cup-shaped cylindrical member 53 having an annular flange 54 adjacent the end thereof. The cylindrical member 53 and annular flange 54 are sized identical to the cylinder 41 and flange 42, respectively, so that they will also be closely accommodated within the slots 34 and 36. Cylinder 53 also has a stepped opening means extending therethrough, which opening means is formed by bores 56 and 57 which are identical to the above-described bores 43 and 44, respectively. A further threaded bore 58 extends through the end wall of the cylinder 53, which threaded bore 58 is aligned and communicates with the bores 53 and 54. Threaded bore 58 is also of a diameter larger than the frit 13 to enable the frit to be pulled into and through the bore 58.

The cylinder member 53 is, in the illustrated embodiment, provided with a plurality of pins 59 fixed thereto and projecting radially therefrom, these pins 59 are used to assist in rotating the extractor guide 17 when desired.

Extractor member 18 is adapted to coact with the cylinder member 53 and, for this purpose, is provided with an externally threaded screw member 61 which is adapted to be threadably engaged within the bore 58. Screw member 61 has an enlarged cylindrical knob or handle 62 secured to the outer end thereof, which handle is preferably knurled to facilitate gripping thereof. A pair of aligned openings 63 and 64 extend coaxially through the extractor member 18, which openings 63 and 64 are of different diameters and are joined by a conical portion 66.

The smaller opening 63 is adapted to slidably accommodate therein an elongated tap 67 of conventional configuration. Tap 67 is interconnected, by means of a conically tapered portion, to an enlarged cylindrical shank 68 which projects through the opening 64 and extends into an opening 69 which extends coaxially through an enlarged handle or knob 71. A conventional set screw 72 is provided for locking the shank 68 of the tap to the handle 71. The handle 71 has a projecting hub portion 73 for a purpose to be explained hereinafter. The handle 71, which can be molded from plastic or other suitable material, is preferably provided with a ribbed exterior surface to facilitate gripping thereof.

OPERATION

The operation of the present invention will be briefly described to ensure a complete understanding thereof.

When the small metal frit 13 is to be removed from the end of the column 12, which end may or may not possess a ferrule 47, the cup-shaped drill guide 14 is slipped over the tube until the end thereof extends into the bore 44 and abuts against the end wall. When so positioned, the frit 13 is substantially aligned with the small bore 46 and the ferrule 47 is accommodated within the large bore 43. The retainer 11, in its open position of FIG. 1, is then moved transversely toward the tube 12 so that the tube 12 enters the axial slot 23 simultaneous with the insertion of the flange 42 into the slot 34. When the tube 12 is seated against the semi-cylindrical wall 24 defined at the bottom of the slot 23, the clamping member 26 is swingably moved into its closed position wherein it extends across the slot 23. The threaded clamping knob 31 is then threaded inwardly on the rod 29 until the surface 32 thereon engages the abutment surface 33 formed on the retainer member 21. The clamping knob 31 is rotated until the clamping member 29 is drawn tightly against the tube 12 for clampingly holding the tube 12 snugly between the semi-cylindrical surfaces 24 and 28. In this locked position of the retainer as illustrated in FIGS. 2 and 3, the tube 12 is thus fixedly held relative to the retainer 11, and the retainer 11 additionally holds the drill guide 14 on the end of the tube substantially as illustrated in FIGS. 2 and 4.

The holder 16 is then positioned so that the drill 48 is slidably inserted through the small bore 46. The holder 16 is manually rotated so that the tip of the drill 48 forms a bore in the frit 13, which bore extends a predetermined distance into the frit. The depth of the bore formed in the frit is determined by the length of the drill 48 which projects beyond the forward end of the holder 51, which length in turn can be selectively adjusted by the set screw 52.

After the above-mentioned bore has been formed in the frit, the drill device 16 is removed. The clamping knob 31 is then threaded outwardly to release the clamping member 26 so that it can be swung into its open position. Retainer 11 is then moved transversely so as to disengage both the tube 12 and the drill guide 14. The drill guide 14 is then removed from the end of the tube 12. The extractor guide 17 is then slidably inserted over the end of the tube 12, and the retainer 11 is again moved transversely into engagement with the tube and the flange 54 on the cup-shaped cylindrical member 53, so that the retainer will again clampingly hold the tube 12 stationary relative thereto, and will additionally hold the guide 17 on the end of the tube substantially as illustrated in FIG. 5.

The extractor member 18 is then threaded into the opening 58 until the end of the screw member 61 substantially abuts the frit 13. When so positioned, the bore previously formed in the frit 13 is aligned with the opening means which extends coaxially through the extractor member 18. The tapping unit 19 is then positioned so that the tap 67 can be slidably inserted through the central opening formed in the extractor member 18. The tap 67 is slidably inserted through the extractor member 18 until the free end of the tap 67 engages the bore formed in the frit 13, which bore is slightly smaller than the thread tap. The handle 71 of the tapping unit 19 is then rotated so as to cause the tap 67 to be threadably engaged with the frit 13, which rotation of the tapping unit also causes it to be pulled axially inwardly. The tapping unit is rotated until the tap 67 extends to substantially the end of the bore formed in the frit 13. When in this position, the hub 73 on the handle is disposed in abutting engagement with the handle 62 of the extractor member 18. This relationship is achieved by loosening the set screw 72 and adjusting the handle 71 axially along the shank 68 and then retightening the screw 72 when the handle is in its desired position.

With the apparatus in the position described above, as illustrated in FIG. 5, the extractor guide 17 and handle 71 are held nonrotatable relative to the tube 12. The handle(s) 59 of the extractor guide 17 is rotated in a direction to cause the screw member 61 to be withdrawn from the bore 58. This rotation of handle(s) 59 causes the extractor member 18 to be moved outwardly (rightwardly in FIG. 5) away from the tube and also causes the tapping unit 19 to be moved outwardly so that the tap 67 imposes an axial pulling force on the frit 13. In this manner, the frit 13 is axially removed from the end of the shaft 12 substantially as illustrated in FIG. 6. Thus, the frit can be removed in a simple and efficient manner without damaging the tube 12, whereupon the tube can thus be reused.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A method of removing a nonthreaded pluglike filter from the end of a tube, comprising the steps of:
    forming a small bore of preselected depth in said filter so that said bore is coaxially aligned with said filter and opens outwardly through one end thereof;
    positioning a guiding member on the end of said tube so that an opening in said guiding member is aligned with said filter;
    axially securing said guiding member relative to said tube;
    rotatably threading a threaded extractor member into the opening formed in said guide member so that a central opening formed in said extractor member is aligned with the bore formed in said filter;
    inserting a thread-forming tap through said central opening until the end thereof is adjacent the bore in said filter;
    then rotating said tap for causing same to be threadably engaged with said filter and for causing said tap to move axially inwardly relative to said central opening until said tap substantially abuts said extractor member; and then
    rotating said extractor member in a reverse direction relative to said guide member for threadably disengaging said extractor member from said guiding member while said extractor member simultaneously imposes an axial pushing force on said tap for pulling the filter from said tube.

2. An apparatus for extracting a small filter which is pressed into the end of a tube, comprising:
    a guide member adapted to be removably mounted on the end of a tube, said guide member having opening means extending therethrough and including a first bore extending inwardly from one end of said guide member for receiving therein the end of said tube, said opening means including a second bore coaxially aligned with said first bore and extending inwardly from the other end of said guide member, said second bore being substantially smaller in cross-section than said first bore, said first and second bores being in open communication with one another and the bottom of said first bore being defined by an end surface which is adapted to abut against the free end of said tube;
    retainer means including relatively movable clamping portions adapted to be disposed in surrounding relationship to said tube for clampingly and fixedly engaging same, said retainer means also including coupling means coacting with said guide member for axially connecting said guide member to said retainer means to axially fix said guide member relative to said tube;

extractor means supported and guided by said guide member and connectible to said filter for removing same from said tube;

said extractor means including an extractor member rotatably supported on said guide member, said extractor member including a rotatable grip portion spaced outwardly from the other end of said guide member and a screw portion disposed within said second bore and threadably engaged with said guide member, said extractor member having a central opening extending therethrough in alignment with said opening means;

said extractor means also including a thread tapping unit having an elongated thread forming tap member positioned within and extending through the central opening in said extractor member, said tap member having one end thereof threadably engaged with said filter, and abutment means coacting between said tap member and said extractor member for limiting the depth to which said tap member can be threaded into said filter whereby rotation of said extractor member relative to said guide member and said tapping unit in a direction for causing said screw portion to be withdrawn from said guide member causes said tapping unit to be moved axially outwardly away from said guide member so that said tap member axially pulls said filter out of said tube.

3. An apparatus according to claim 1, wherein said guide member is substantially cylindrical and includes an enlarged annular flange adjacent said one end thereof, said retainer means including a retainer member having an axially elongated slot formed therein for accommodating said tube, and said coupling means comprising a slot which is disposed adjacent one end of said retainer member and extends radially outwardly through the periphery thereof, said slot being sized to slidably but snugly accommodate therein the annular flange on said guide member.

4. An apparatus according to claim 3, wherein said retainer member defines one of said clamping portions thereon, and the other of said clamping portions being hingedly connected to said retainer member for swinging movement toward and away from said one clamping portion, said clamping portions having opposed substantially semi-cylindrical walls thereon adapted to snugly embrace and clampingly engage the outer surfaces of said tube, and releasable holding means coacting between said retainer member and said swingable clamping portion for fixedly connecting same together in surrounding and clamping relationship to said tube.

5. An apparatus according to claim 4, wherein said first bore is defined by first and second openings which are coaxially aligned, said first opening extending inwardly from said one end of said guide member and being of a diameter larger than said second opening, said second opening being disposed adjacent the inner end of said first bore, said second opening being of a diameter similar to the diameter of said tube, and said first opening being of a diameter substantially larger than said tube so as to accommodate therein a ferrule on said tube.

6. An apparatus according to claim 4, wherein said second bore is threaded and is of a diameter larger than said filter, and wherein said abutment means comprises an enlarged handle secured to the other end of said tap member, whereby the grip portion of said extractor member is disposed between said other end of said guide member and said handle.

7. An apparatus according to claim 4, including a drill guiding element adapted to be movably mounted on the end of said tube, said drill guiding element having hole means extending therethrough and defined by a first hole extending inwardly from said one end of said guiding element for receiving therein the end of said tube and a second hole extending inwardly from the other end of said guiding element in coaxial alignment and communication with said first hole, said second hole being substantially smaller in cross section than said first hole and also being smaller in cross-section than said filter, said first and second holes being aligned with said filter when said guiding element is mounted on said tube;

said guiding element including means associated therewith and coacting with said coupling means for permitting said guiding element to be axially fixed on said tube by said retainer means; and a drill unit for forming a bore within said filter, said drill unit including an elongated rotatable holder and a drill projecting outwardly from one end of said holder and adapted to be slidably guided through said second hole for engagement with said filter.

* * * * *

UNITED STATES PATENT OFFICE
CERTIFICATE OF CORRECTION

Patent No. 3,978,575            Dated September 7, 1976

Inventor(s) William F. Beyer and Harry S. Dankert

It is certified that error appears in the above-identified patent and that said Letters Patent are hereby corrected as shown below:

Column 7, line 34; change "claim 1," to ---claim 2,---.

Signed and Sealed this

Thirtieth Day of November 1976

[SEAL]

*Attest:*

RUTH C. MASON
*Attesting Officer*

C. MARSHALL DANN
*Commissioner of Patents and Trademarks*